US010125311B1

(12) United States Patent
Meylemans et al.

(10) Patent No.: US 10,125,311 B1
(45) Date of Patent: Nov. 13, 2018

(54) FUNCTIONALIZED FLUORESCENT NANOPARTICLES, METHODS OF SYNTHESIS AND METHODS OF USE

(71) Applicant: The United States of America as Represented by the Secretary of the Navy, Washington, DC (US)

(72) Inventors: Heather A. Meylemans, Ridgecrest, CA (US); Lee R. Cambrea, Ridgecrest, CA (US); Madeline Kooima, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 133 days.

(21) Appl. No.: 15/072,692

(22) Filed: Mar. 17, 2016

Related U.S. Application Data

(60) Provisional application No. 62/135,822, filed on Mar. 20, 2015.

(51) Int. Cl.
*G01N 21/64* (2006.01)
*G01N 33/20* (2006.01)
(Continued)

(52) U.S. Cl.
CPC ........ *C09K 11/623* (2013.01); *G01N 21/6428* (2013.01); *G01N 21/643* (2013.01);
(Continued)

(58) Field of Classification Search
CPC .. G01N 21/64; G01N 21/6428; G01N 21/643; G01N 21/6447; G01N 21/78; G01N 33/18; G01N 33/1813; G01N 33/182; G01N 33/20; G01N 31/22; Y10T 436/18; Y10T 436/188
(Continued)

(56) References Cited

U.S. PATENT DOCUMENTS 6,114,038 A * 9/2000 Castro ...................... B82Y 5/00
257/614
2004/0247861 A1* 12/2004 Naasani ................. B82Y 15/00
428/336
(Continued)

OTHER PUBLICATIONS

Chen et al. Applied Mechanics and Materials, ISSN: 1662-7482, vols. 284-287, Jan. 25, 2013, pp. 138-142.*
(Continued)

*Primary Examiner* — Maureen Wallenhorst
(74) *Attorney, Agent, or Firm* — Stuart H. Nissim

(57) ABSTRACT

A method for the fluorescence detection of metal ions and other environmental hazards utilizing ligand functionalized fluorescent nanoparticles. Synthesis of the non-toxic, air, and water stable nanoparticles has been optimized. The fluorescent nanoparticles of the present invention are made from varying ratios of metals including zinc, silver, copper, and indium and sulfur. By varying the ratios of these metals we are able to synthesize nanoparticles that emit over a large range of the visible spectrum. Charge transfer between a target molecule and the nanoparticle is readily identified by a fluorescence change allowing for a fast, simple, visual detection system without the need for expensive analytical instrumentation.

15 Claims, 5 Drawing Sheets

(51) Int. Cl.
 *G01N 33/18* (2006.01)
 *G01N 31/22* (2006.01)
 *C09K 11/62* (2006.01)

(52) U.S. Cl.
 CPC ......... *G01N 31/22* (2013.01); *G01N 33/1813* (2013.01); *G01N 33/20* (2013.01); *G01N 2021/6432* (2013.01); *G01N 2201/068* (2013.01)

(58) Field of Classification Search
 USPC ... 436/73, 77, 79, 80, 81, 84, 119, 123, 164, 436/166, 172; 422/82.05, 82.08
 See application file for complete search history.

(56) References Cited

U.S. PATENT DOCUMENTS

2008/0153085 A1* 6/2008 Patolsky .................. B82Y 5/00
 435/6.11

2014/0284528 A1* 9/2014 Yukawa ............... G01N 33/582
 252/519.4

OTHER PUBLICATIONS

Xiong et al. Journal of Materials Chemistry B, vol. 1, 2013, pp. 4160-4165.*
Uematsu et al. Chemical Communication, 2009, pp. 7485-7487.*
Mandal et al. Analyst, vol. 137, 2012, pp. 765-772.*
Shinchi et al. Bioconjugate Chemistry, vol. 25, Jan. 19, 2014, pp. 286-295.*
Ali et al. Analytical Chemistry, vol. 79, 207, pp. 9452-9458.*
Ke et al. Scientific Reports, vol. 4:5624, Jul. 9, 2014, pp. 1-6.*
Kameya et al. Sensors and Actuators B: Chemical, bol. 190, Aug. 13, 2013, pp. 70-77.*
Zhang et al. Analytical Chemistry, vol. 86, Oct. 30, 2014, pp. 11727-11733.*
Subramaniam, P., et al., "Generation of a Library of Non-Toxic nanoparticles for Cellular Imaging and siRNA Delivery", Adv. Mater., 2012, 4014-4019, 24, US.

* cited by examiner

FUNCTIONALIZED FLUORESCENT NANOPARTICLES, METHODS OF SYNTHESIS AND METHODS OF USE

CROSS-REFERENCE TO RELATED APPLICATIONS

This is a non-provisional application claiming the benefit of parent application Ser. No. 62/135,822 filed on Mar. 20, 2015, whereby the entire disclosure of which is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to the synthesis and use of functionalized fluorescent nanoparticles.

BACKGROUND OF THE INVENTION

Fluorescent nanoparticles, and their subclass of quantum dots, have been explored for many potential applications including: high efficiency solar panels, LEDs (light emitting diodes), flexible and brighter displays, advanced bioimaging, and biosensing techniques. Most of these potential applications utilize nanoparticles that are unstable in environmental conditions thus requiring sealed (from air and water) systems and careful treatment to avoid oxidation and deterioration. An additional problem with current nanoparticles is that they are made with toxic metals such as cadmium, selenium, lead, or tellurium. The combination of toxicity and instability limit potential nanoparticle uses outside of a laboratory environment.

Nanoparticles characterized as quantum dots are defined as particles that have a radius of less than 100 nanometers. They can be as small as 2 to 10 nanometers, corresponding to 10 to 50 atoms in diameter and a total of 100 to 100,000 atoms within the volume of a quantum dot. A quantum dot confines the motion of conduction band electrons, valence band holes, or excitons (bound pairs of conduction band electrons and valence band holes) in all three spatial directions. As a result, these particles exhibit optical and thermal properties which are different from those of the bulk material from which they are made. Quantum dots can show strong quantum confinement effects; they exhibit an inherent fluorescence color—they emit a particular color upon being illuminated by UV light—based on their energy band gap which is controlled by the crystal size and chemical composition. For instance, CdSe covers the whole visible range: the 2 nm diameter CdSe quantum dot emits in the blue range and a 10 nm diameter CdSe quantum dot emits in the red range. The ability to tune the emission spectrum of these nanoparticles throughout the visible region gives researchers an ability to customize the molecules to fit their application.

Toxicity and environmental stability of nanoparticles are particularly important for biological applications such as the detection of tumors and other medical related biosensing applications. Nanoparticles made from zinc, silver and indium have been suggested for these applications (Subramaniam, P., et al., "Generation of a Library of Non-Toxic nanoparticles for Cellular Imaging and siRNA Delivery", Advanced Materials, 2012, 24, 4014-4019); however, attempts to duplicate this disclosed synthesis and confirm the resulting particles have been unsuccessful. Other work has also demonstrated coupling between CdSe—CdS core-shell quantum dots, enclosed in a silica shell, and biological molecules (Brunchez et al., "Semiconductor nanocrystals as fluorescent biological labels", Science, 281: 2013-2016 (1998)). Similarly, highly fluorescent nanoparticles (zinc sulfide-capped cadmium selenide) have been covalently coupled to biomolecules for use in ultrasensitive biological detection (Warren and Nie (1998) Science, 281: 2016-2018).

Other uses for nanoparticles include other sensing applications—such as metal detection in water—as their fluorescence intensity has been shown to depend on environmental conditions. The ability to identify contamination in a variety of water sources quickly and inexpensively would greatly help in many different circumstances. Metal contamination in storm water runoff and near shipyards is of great interest for protection of our environment. These types of contamination occur at discrete time points with a limited window to identify the problem before the sample is diluted into the main water stream. If a quick, easy analytical method to indicate if contaminated water may have been released into streams or oceans existed, then more frequent testing could be performed in-situ and many pollution problems could be mitigated.

Currently, the state of the art technique for metal detection in water is inductively coupled plasma mass spectrometry (ICP-MS) which requires samples to be gathered and sent to a laboratory for testing. Although a very accurate and quantitative method, this technique has several drawbacks. The largest drawback being the size and expense of the instrument itself. ICP-MS is not a field portable technique and therefore samples must be collected and transferred back to the laboratory for analysis, a very time consuming task. Samples must also be free from particulates to avoid disrupting flow or blocking the nebulizer. Additionally, continuously running samples with high salt concentrations (like seawater) can eventually lead to blockages. These blockages can be avoided by diluting samples but this begins to affect detection limits and takes time and careful laboratory work.

In contrast to the complicated ICP-MS technique, the presence of metal ions in solution has been shown to influence nanoparticle fluorescence either through a quenching or an enhancement of the nanoparticle fluorescence and thus a potential method of testing. There are several proposed mechanisms for these interactions but the most common mechanism stems from an interaction of the metal ion with a specialized ligand to create a new complex that influences the emission. Specifically, the ligand may recombine with the metal ion leaving behind a surface defect on the nanoparticle which leads to quenching of fluorescence. This quenching process allows for a visual confirmation that a metal ion is present.

These types of quenching interactions between nanoparticles and metal ions have been shown in several types of nanoparticle systems. The most common of these systems are made with toxic materials such as cadmium and either tellurium or selenium. Currently, the most commonly used materials for metal detection applications are lead sulfide, cadmium sulfide, lead selenide, and cadmium selenide. They also frequently use thiol containing ligands such as glutathione (GSH), L-Cysteine (Cys), mercaptoacetic acid (MAA), mercaptopropionic acid (MPA), or mercaptosuccinic acid (MSA) which aide in solubility as well as metal ion affinity. Most of these systems utilize ligands for specific binding of metals to nanoparticles such as using a thiol containing ligand to bind mercury. J. Ke, X. Li, Q. Zhao, Y. Hou, J. Chen, "Ultrasensitive nanoparticle Fluorescence quenching Assay for Selective Detection of Mercury Ions in Drinking Water", Sci. Rep. 2014, 4, 5624; and, E. M. Ali, Y. Zheng, H. Yu, J. Y. Ying, "Ultrasensitive $Pb^{2+}$ Detection by Glutathione-Capped nanoparticles", Anal. Chem. 2007, 79, 9452-9458. Although some of these systems show great sensitivity for metal ions with detection limits as low as $10^{-11}$ M, they are limited to laboratory use due to the toxicity of the nanoparticles themselves.

The present invention provides a simple, easily scaled process for producing fluorescent nanoparticles, including quantum dot nanoparticles that are relatively non-toxic and environmentally stable in both air and water. These nanoparticles are made from less toxic metals including but not limited to zinc, silver, indium, and copper. Interaction between the nanoparticles and a target analyte (particularly metal ions, both cations and anions) are used for sensing applications. In contrast to current nanoparticle systems, the nanoparticle systems of the present invention lend themselves well to testing in a non-laboratory environment as they are relatively non-toxic and environmentally stable in both air and water. The current invention encompasses several methods of detection including: shifting of the wavelength of fluorescence, an enhancement of fluorescence, or a quenching of fluorescence when a specific target element or molecule is present.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Figure 1:
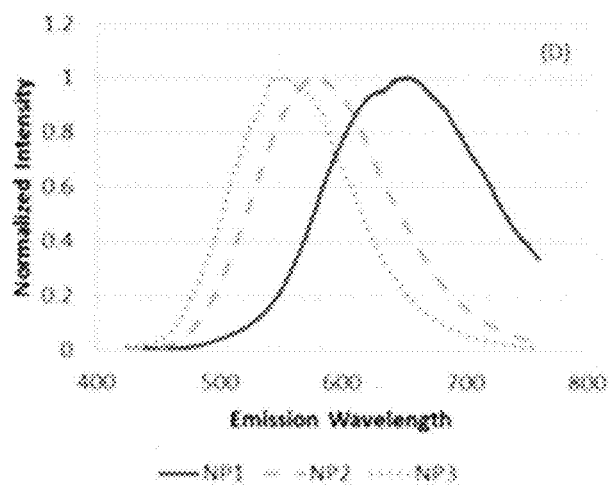
FIG. 1 is a graph of emission spectra collected from 425 nm-775 nm of functionalized nanoparticles excited at 395 nm according to embodiments of the invention.

Although embodiments of the invention are described in considerable detail, including references to certain versions thereof, other versions are possible. Therefore, the spirit and scope of the appended claims should not be limited to the description of versions included herein.

Where a range of values is provided, it is understood that each intervening value, to the tenth of the unit of the lower limit unless the context clearly disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Embodiments of the invention generally relate to colorimetric detection using specifically functionalized, environmentally stable fluorescent nanoparticles, a novel method of producing fluorescent nanoparticles, including quantum dots, a method for creating test strips for metal detection using the fluorescent nanoparticles; and coatings incorporating the fluorescent nanoparticles. These nanoparticles have potential for a number of naval applications particularly in the areas of biofouling and condition based maintenance through the visible fluorescence detection of trace metals. The nanoparticles of the present invention lend themselves well to their use in a non-laboratory environment using various combinations of zinc, silver, indium, copper, and sulfur to create non-toxic, air and water stable fluorescent nanoparticles useful, for example, for metal ion detection in water either in solution or as test strips. Other uses include using the nanoparticles to make coatings and paints for applications such as safety paint on rotor blades of helicopters to make them more visible at night or to make coatings that could be used for commercial applications such as on road signs.

Traditional quantum dots and other fluorescent nanoparticles are not compatible outside of a laboratory environment due to their toxicity and instability. This invention embodies functionalized nanostructures in various spatial layouts such as nanocrystals, nanoparticles, and quantum dots that are air and water stable and non-toxic. Energy transfer upon target binding provides a designer, colorimetric sensing mechanism.

The fluorescent nanoparticles of the present invention are stable as an aggregated solid (in the solid phase), suspended or tethered onto various substrates, or in solution which can then be further formulated into films or coatings. These coatings differ from previously studied polymer nanoparticle hybrids in that they are designed to be the outer shell or paint layer with direct environmental exposure and therefore meeting the requirement that the coatings must be stable in environmental conditions.

If the functionalizing ligand and nanoparticle are properly matched it is possible to tune the fluorescence and/or changes in fluorescence in the presence of just one or a few select targets. This selective fluorescence can be used for an instant-read visual test to detect in real time the contamination of metal ions, for example, in relevant environmental samples. Additionally, synthesizing a series of nanoparticles with identical non-specific ligands shows that metal specificity can be gained strictly from interaction with the nanoparticle core. Direct interaction between metal ions and the nanoparticle core will lead to a simpler, more robust, system.

The metal ion selectivity of the nanoparticles of the present invention can be used to create a test that can easily be performed in the field during an operation (construction, maintenance, repair, general industrial processes, etc.) without needing expensive analytical equipment or pretreatment of samples before analysis. For such a field-able colorimetric test, the fluorescence change must be strong enough that it is visible by eye. Testing could then determine the presence or absence of a particular metal ion by simply combining the nanoparticles with a sample of the water to be tested. The combination of the nanoparticles and the sample could occur in the liquid state by mixing two solutions or in the solid/liquid state by incorporating the nanoparticles into a solid test strip to be dipped into the water to be tested. For example, this solid test strip could be a filter type material or a polymer matrix that encapsulates the nanoparticles (coating type). The resulting fluorescence (i.e., presence, absence, or change therein) under ultraviolet light after combination, will determine the presence or absence of specific contaminants leading to an instant-read, real-time visual test.

One preferred embodiment comprises fluorescent nanoparticles comprised of combinations of two or more components selected from the group consisting of Zinc, Silver, Copper, Indium, Sulfur, and various combinations thereof. Other preferred embodiments comprise two or more components selected from the group consisting of Zinc, Silver, Indium, and Sulfur (ZAIS); although, other non-toxic environmentally stable formulations can be synthesized and used.

Still further preferred embodiments comprise fluorescent nanoparticles (including quantum dot nanoparticles) comprised of combinations of three or more components selected from the group consisting of Zinc, Silver, Copper, Indium, Sulfur, and various combinations thereof.

Another embodiment of the present invention comprises a simple, optimized method of nanoparticle synthesis and functionalization. A preferred method of synthesizing functionalized nanoparticles comprises:

1) combining metals and sulfur at specific molar ratios to get a starting metal powder which is stirred in water at room temperature for about 15 minutes, then filtered and dried under vacuum at about 40° C. for about 12 to about 24 hours;

2) heating the starting metal powder alone in an inert atmosphere for between about 1 and about 60 minutes at about 150° C. to about 250° C.;

3) adding a specified ligand having desired target binding functionality and reacting via further heating at about 150° C. to about 250° C. for between about 1 to about 30 minutes; and, 4) isolating the resulting functionalized nanoparticles using one or more series of centrifuging and washing steps. Each centrifuging is performed for about 5 to about 15 minutes at 2000-10,000 rpm, preferably at greater than about 5000 rpm. Higher centrifugation rates facilitate the isolation of smaller nanoparticles, including quantum dots.

The process described above is improved over previous methods as it better allows for industrial applications and scale-up; as well as for easy manipulation of the metal ratio and ligand functionality for a variety of different applications. Step 1 can be done in bulk and the product stored. Then, as specific applications arise, the product of step 1 can be functionalized with any variety of ligands in step 2 to produce a desired product based upon the application of metal detection, coatings, or test strip applications.

Examples of suitable sources of metal(s) include, but are not limited to, elemental metal and metal salts, including for example, nitrates, phosphates, stearates, sulfates, acetates, and halides. Preferred metal sources include nitrates.

Examples of suitable sources of sulfur include, but are not limited to, diethyldithiocarbamate and sodium sulfide.

Varying the ratio of the metal components Zn:Ag:In:Cu results in changing the wavelength of fluorescence. A preferred embodiment comprises a ratio of xZn:yAg:2yIn. Another preferred embodiment comprises a ratio of $2*(1-x)$Zn:xAg:xIn. In preferred embodiments, the sulfur source is added in an amount of between about 2x to about 5x.

With specific metal ratios in the nanoparticles and the selection of a proper ligand, a system can be created for a selective colorimetric sensor.

In a preferred synthesis temperatures for heating are between about 150° C. to about 250° C., more preferably between about 170° C. to about 200° C.

In a preferred synthesis a stoichiometric excess of ligand is added. Preferably a large excess of ligand, on the order of at least 2x-30x. Any excess ligand that doesn't bind is removed during centrifugation and washing. In one alternate embodiment of the synthesis, the ligand is used as a solvent in the process.

Although embodiments of the invention are described in considerable detail, including references to certain versions thereof, other versions are possible. Examples of other versions include various ratios of Zn:Ag:In:Cu:S (where the amount of any particular component may equal zero); a variety of functionalizing ligands, and any number of polymer compositions for coating/films. Therefore, the spirit and scope of the appended claims should not be limited to the description of versions included in the specific examples herein.

EXAMPLES

Example 1

A number of powders were made by combining sources of four elements—zinc, silver, indium, and sulfur, by adding the metals in a ratio of $2*(1-x)$Zn, xAg, xIn, and a stoichiometric excess of sulfur, in water and stirring at high speed between 500-1200 rpm for between 1-60 minutes at room temperature. The starting metal source materials used were $Zn(NO_3)_2$, $AgNO_3$, and $In(NO_3)_3$, and diethyldithiocarbamate as the sulfur source.

Example 2

A number of powders were made by combining the four elements—zinc, silver, indium, and sulfur—by adding 2-4 mmol of each metal in a ratio of $2*(1-x)$Zn:xAg:xIn and 2-10 mmol of sulfur in 20 mL water and stirring at high speed for 5 minutes. The starting materials used were Zn(NO$_3$)$_2$, AgNO$_3$, In(NO$_3$)$_3$ and diethyldithiocarbamate (as the sulfur source) and they were added as outlined in Table 1 for the samples.

TABLE 1

Sample Preparation for Nanoparticle Synthesis

| Sample ID | Ratio used Zn:Ag:In:S |
|---|---|
| NP1 | 0:1:1:2 |
| NP2 | 0.6:0.7:0.7:2 |
| NP3 | 1.2:0.4:0.4:2 |

Each powder was then filtered through a medium porosity frit and washed with water and methanol. Each powder was dried overnight in the oven at 40° C.

After drying overnight, 50 mg of powder was placed in a flask and heated to 180° C. After heating for 30 minutes, 1 ml of dodecylamine ligand was added and the mixture heated for a further 3 minutes. The resulting liquid was centrifuged at 5000 rpm for 15 minutes. The supernatant was removed and washed with methanol and centrifuged again at 5000 rpm for 15 minutes. The supernatant was removed and the precipitate dissolved in 10 mL of chloroform or DMSO depending upon the desired final solution.

A primary function of a suitable ligand for the present invention is that it binds to the target compound and facilitates the appropriate electrical effect upon binding, i.e., charge transfer between the target ion/molecule and the nanoparticle. Preferred ligands include, for example, hetero-straight chain, hetero-cyclic, or hetero-aromatic compounds having up to about 20 carbon atoms and having one or more hetero atoms, where the hetero atoms are independently selected from N, S, O, P, and combinations thereof. Examples include, but are not limited to, dodecylamine, dodecane thiol, phenanthroline, bipyridine, and thiocyanate.

Example 3

By changing the ratio of zinc, indium and silver; nanoparticles, in the quantum dot size range, that emit across the entire visible spectrum were made. These examples all utilized dodecylamine as the ligand. For this set of samples, the amount of indium and silver was kept the same (x) and the amount of zinc was varied as 2*(1−x). The amount of sulfur in the samples was equimolar with the total metal concentration. Three different samples were synthesized, characterized, and tested. The ratios and emission wavelength are shown in Table 2.

TABLE 2

Sample Preparation for nanoparticle Synthesis

| Sample ID | Ratio used Zn:Ag:In:S | Zn (mmol) | Ag (mmol) | In (mmol) | S (mmol) | $\lambda_{max}$ (excited @ 395 nm) |
|---|---|---|---|---|---|---|
| NP1 | 0:1:1:2 | 0.00 | 0.63 | 0.63 | 2.49 | 647 nm |
| NP2 | 0.6:0.7:0.7:2 | 0.38 | 0.44 | 0.44 | 2.49 | 578 nm |
| NP3 | 1.2:0.4:0.4:2 | 0.75 | 0.25 | 0.25 | 2.49 | 549 nm |

Example 4

Each of the nanoparticle samples from Example 3 were characterized using energy dispersive spectroscopy (EDS), UV-Vis and fluorescence. While EDS is not a quantitative technique it showed that all of the expected elements were present in the samples. UV-Vis spectra were collected for each of the samples from 250-800 nm and the absorbance for all three samples lies in the UV region of the spectrum below 450 nm. The samples were each excited at 395 nm and the emission spectra were collected from 425 nm-775 nm (FIG. 1) with emission maximum (λmax) reported in Table 2. Comparisons of relative fluorescence intensity, in the presence of metal ions, were determined at λmax throughout.

Example 5

Figure 2:
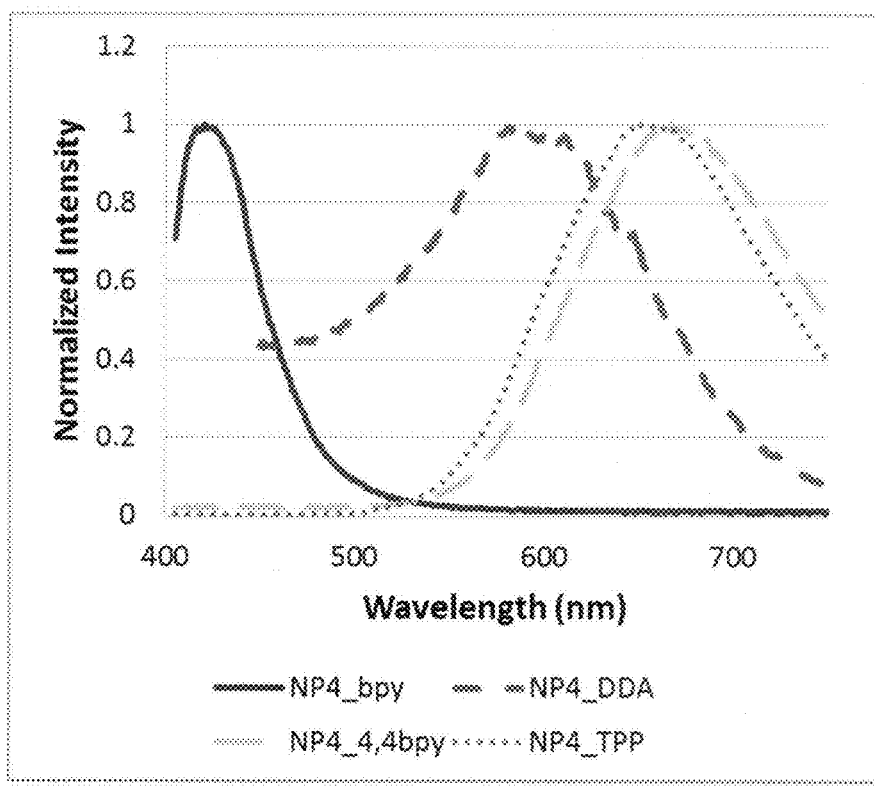
FIG. 2 is a graph of emission spectra of samples of a nanoparticle with a variety of ligands according to embodiments of the invention.

Using one selected ratio of metals (sample NP4—Zn:Ag:In of 1:1:2), a variety of ligands were used to synthesize a set of quantum dots that fluoresce over a wide range of the visible spectrum, as shown in FIG. 2.

Example 6

A series of metal ions, was selected for testing based on known environmental hazards or of general interest. The metals Al(SO$_4$)$_3$.18H$_2$O, CoCl$_2$.6H$_2$O, CuCl$_2$, FeCl$_3$, HgCl$_2$, K$_2$CrO$_7$, KCrO$_4$, MnCl$_2$, and Pb(NO$_3$)$_2$ were obtained from Sigma Aldrich. Solutions of metal ions were made by preparing a stock solution with a concentration of 5 mM and then making serial dilutions to create concentrations of 0.5 mM, 50 mM, 5 μM and 500 nM (~1 ppm). Metal ions were dissolved in deionized water to known concentrations before testing. All solutions were prepared from chloride salts, except for the chromate and dichromate, lead, and aluminum samples, which were potassium, nitrate, and sulfate salts, respectively. Each of these metals were made and tested in water at five different concentrations made via serial dilution in a range of 5 mM-500 nM.

Samples used to measure the response of the nanoparticle fluorescence in the presence of metal ions were prepared by using 3 mL of the desired metal ion solution and adding in 1 mL from a stock solution of nanoparticles. Emission spectra were then collected immediately after mixing of the two solutions. The measurements are reported by comparing the resulting fluorescence intensity (E) after addition to metal ions to the initial fluorescence intensity (E0) before metal ion exposure. Depending on the sensitivity of the nanoparticle to a particular metal the sample can appear to be unreacted (E/E0 of 1.0), completely reacted and no fluorescence detected by eye (E/E0 of 0.2 or less) or partially reacted where fluorescence is visible but weaker than the starting intensity (E/E0 of ~0.4-0.8). To categorize these three regimes is fairly straightforward by eye without the need for additional instrumentation to actually measure the fluorescence.

Laboratory testing of the three nanoparticle samples with various metal ions was conducted by visual inspection and then fluorescence measurements were taken to determine the fluorescence remaining compared to the starting nanoparticle sample (E/E0). Data reported in the charts and tables are reported at the emission maximum (λmax) for each of the nanoparticle samples without metal ions as reported in Table 2.

Figure 3:
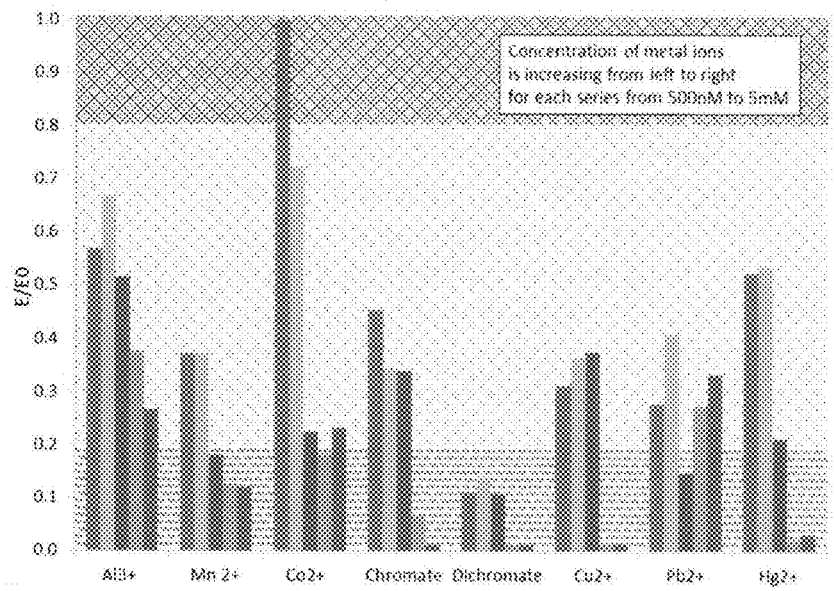
FIG. 3 is a graph of changes in emission intensity of nanoparticles exposed to various concentrations of a number of metals according to embodiments of the invention.

In FIG. 3, NP1 showed the reaction trend, where fluorescence becomes more quenched as the concentration of metal ions is increased, for most of the metal ions. There were however a few exceptions to this, in particular chromate and to a greater extent dichromate. The reaction of NP1 with dichromate led to a complete quenching of fluorescence at concentrations as low as 500 nM. Interestingly, chromate despite being the same metal, in the same oxidation state did show some fluorescence at these lower concentrations from 50 μM to 500 nM, while concentrations higher than 50 μM did quench the fluorescence in this sample. These results were unexpected given the generality of the dodecylamine ligand, but may point toward metal ion size or overall charge having an effect on selectivity. The other observation that was unexpected, and can be seen in the data is that the level of quenching is not linear with these samples. There is clearly a threshold where there is little to no interaction with the nanoparticle and then the interaction is drastic and the sample is quenched. This is seen most obviously in both the $Cu^{2+}$ and $Hg^{2+}$ solutions. In both cases at a concentration of 5 μM or greater the sample is quenched. This characteristic could be useful in determining not only which metals are present in solution but also help to give some indication of the concentration of that metal as well.

Figure 4:
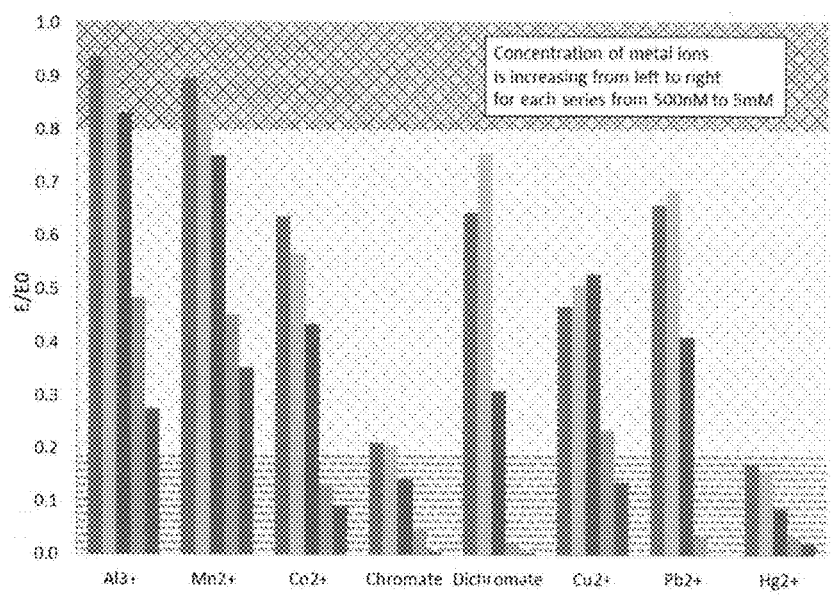
FIG. 4 is a graph of the selectivity of changes in emission intensity of nanoparticles exposed to various concentrations of a number of metals according to embodiments of the invention.

Testing of NP2 was expected to look the same as NP1 given that the ligand surrounding the metal core was again dodecylamine. No selectivity was anticipated and yet NP2 not only showed selectivity for certain metal ions, the selectivity was different than that seen in NP1 (FIG. 4).

NP2 showed a significant selectivity for mercury ions in solution. This result is the opposite of the reaction with $Hg^{2+}$ seen in NP1 where mercury was the least reactive metal that was tested. For solutions containing concentrations of $Hg^{2+}$ ions as low as 500 nM the solution is completely quenched (as determined by eye) for NP2. This was also true for chromate when the NP2 solution was used for the test. And, as seen with NP1 the detection of dichromate and chromate are different.

Figure 5:
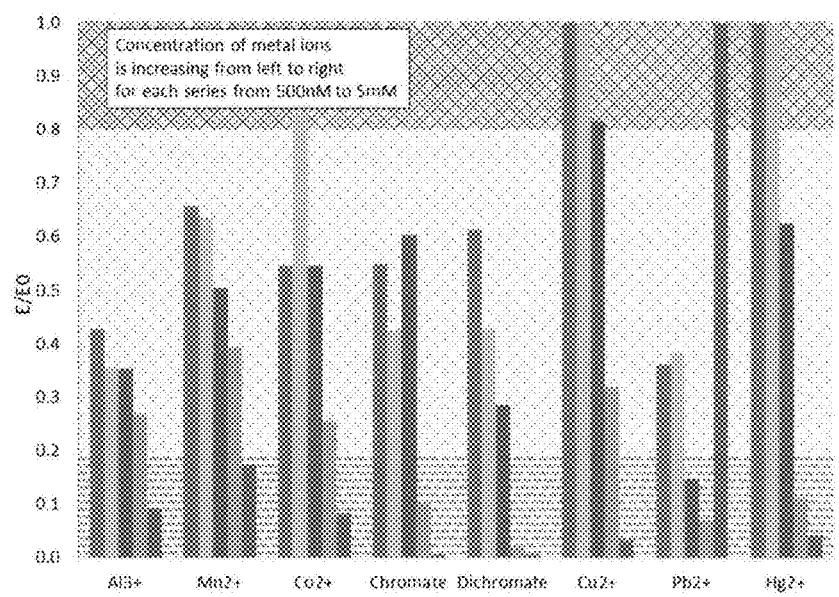
FIG. 5 is a graph of the absence of selectivity of changes in emission intensity of a sample of nanoparticles exposed to various concentrations of a number of metals according to embodiments of the invention.

In contrast to both of the other nanoparticle samples, NP3 appears to have no selectivity for any particular metal ion in water. The NP3 sample shows the most consistent response to each metal ion, showing a general trend of quenching as the concentration of metal ions increase (FIG. 5). NP3 is the only sample in which all of the different ions completely quench the sample at a concentration of 5 mM or greater, this may be a good configuration to use in the lab as a reference system. Similarly, once the concentration of the metal ions drops lower than 5 μM the fluorescence is visible regardless of the metal ion, there is no selectivity in NP3.

Example 7

Figure 6:
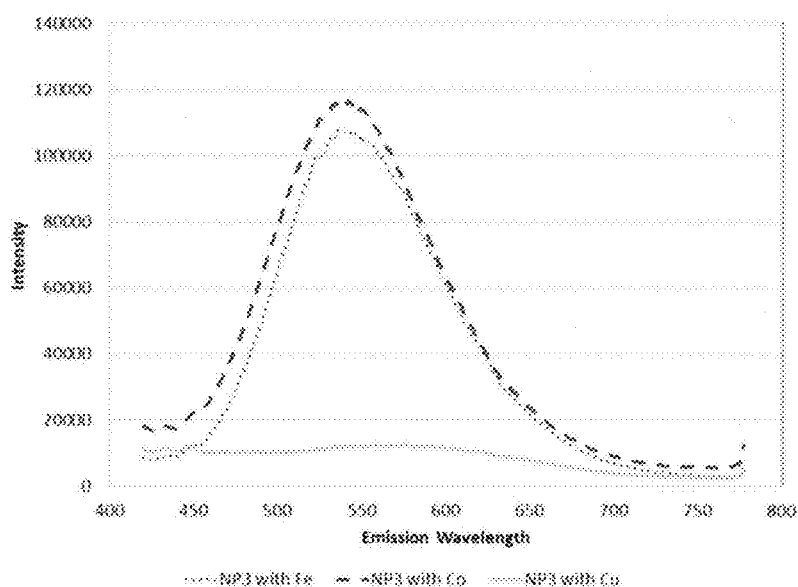
FIG. 6 is a graph showing a selective preference for $Cu^{2+}$ ions over other metals in a change in emission intensity in nanoparticles according to embodiments of the invention.

A set of experiments was performed with metal ions in acetonitrile solutions, and the nanoparticles dissolved in chloroform. Using these solvents, under these conditions, the nanoparticles do not aggregate or precipitate from solution. Generally there was no significant change to the fluorescence upon exposure to the metal ions; however, the exception to this was the preference for $Cu^{2+}$ ions over the other metals. Even with $Cu^{2+}$ concentrations as low as 500 nM (~1 ppm) the NP3 fluorescence was completely quenched (FIG. 6).

Example 8

Figure 7:
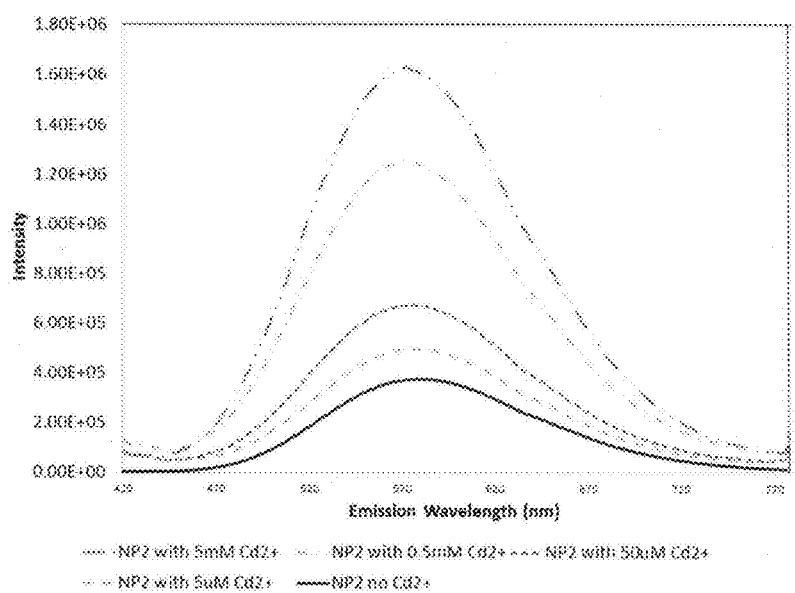
FIG. 7 is a graph showing an increase in emission intensity in the presence of increased concentrations of cadmium ($Cd^{2+}$) ions in nanoparticles according to embodiments of the invention.

All three nanoparticle samples (NP1, NP2, and NP3) had the opposite reaction when tested with cadmium ($Cd^{2+}$) ions. In this case, as the concentration of cadmium in solution increased the fluorescence of the nanoparticles was enhanced rather than quenched as seen with all other metals tested. FIG. 7 shows the emission spectra of NP2 with various concentrations of $Cd^{2+}$ ions. The fluorescence increases by nearly an order of magnitude when compared with NP2 in the absence of $Cd^{2+}$. This order of magnitude increase is seen for all three of the nanoparticle samples in the presence of cadmium.

Example 9

Various ligands can be produced and tested with the nanoparticle powders. Examples of such preferred ligands include, but are not limited to:

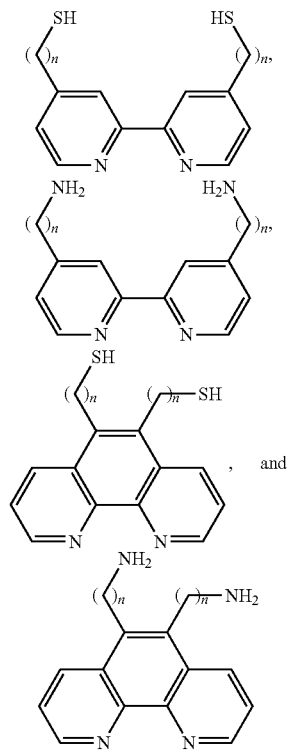

where

is an alkyl having 1-20 carbon atoms.

Example 10

A thiol ligand is synthesized using the method comprising:

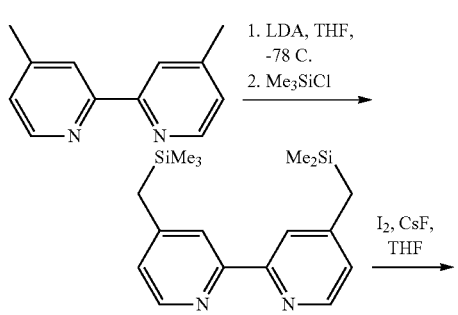

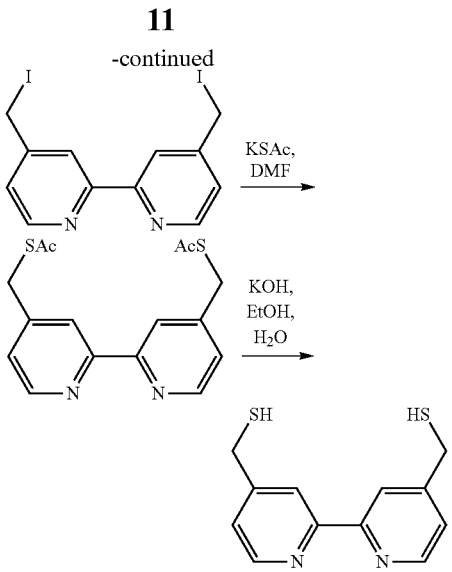

When specific ligands are added to the nanoparticle powders, the resulting fluorescent nanoparticles become functionalized to specifically bind target molecules. Upon binding of the target molecules to the nanoparticles, a shift in emission wavelength is observed (for example the solution turns from blue to red). The extent of this wavelength shift will depend upon the charge transfer interaction between the target molecule and nanoparticle, conducted through the ligand.

Example 11

Using three nanoparticle compositions from Example 2, tests were run with sea water obtained from the Santa Barbara, Calif. area. The seawater was first tested using ICP to determine the natural abundance of ions in the seawater and compared to widely accepted values (Table 3). The seawater sample was in good agreement with expected values with only the amount of vanadium being slightly elevated. The nanoparticle samples were added in the absence of any known metal contamination and emission spectra were collected to determine if the nanoparticles continue to fluoresce given the natural makeup of the sea water. The emission spectra show that the sea water had no effect on the fluorescence of the nanoparticles showing that these nanoparticles function in real life environmental situations without any pretreating of the sample.

TABLE 3

Ions Present in Sea Water at greater than 3 ppm

| Ion | Santa Barbara Concentrations (mg/mL) | Typical Concentrations (mg/mL) |
|---|---|---|
| Sodium | 10,230 | 10,800 |
| Magnesium | 1,255 | 1,290 |
| Calcium | 403 | 411 |
| Potassium | 372 | 392 |
| Strontium | 5.82 | 8.10 |
| Boron | 3.55 | 4.45 |
| Vanadium | 3.08 | 0.002 |

Another embodiment of the present invention comprises the formulation of optical or sensing coatings incorporating fluorescent nanoparticles. In preferred embodiments these nanoparticles comprise the quantum dots/nanoparticles of the current invention. Such coatings can be used for optical and/or sensing functions. These nanoparticles can be incorporated into a coating for increased situational awareness. The coating can be made either as water dispersible or a solvent dispersible system depending upon needs for the application. It is formed by mixing a polymer with the fluorescent nanoparticles by standard polymer processing techniques. The ratio of florescent nanoparticles to polymer (fill factor) may range from 0.1-90% nanoparticles depending on the application. Various polymers including, but not limited to, Nylon, cellulose triacetate, poly(lauryl methacrylate) (PLMA), poly(methyl methacrylate) (PMMA), and biphenyl perfluorocyclobutyl (BP-PFCB) can be used. The preferred polymer coating protects and stabilizes the nanoparticles in the environment but also should not interfere with absorption of light or the resulting fluorescence emission of the nanoparticles. Methods for applying the coating to an object of interest include but are not limited to layer by layer, spraying, electrostatic coating, painting, dip coating, spin casting, powder coating and alternating polyelectrolyte deposition.

Example 12

Nanoparticles prepared as described in Example 2 were made and dissolved in a solution of chloroform (100 mg/20 mL concentration). Less than 1 mL of solution was added to about 100 mg of polymethyl methacrylate (PMMA) to form a fluorescent liquid that was drop coated onto a glass substrate and quickly cured at room temperature to get a fluorescent coating that was water resistant and remains fluorescent for longer than 1 month.

Example 13

Figure 8:
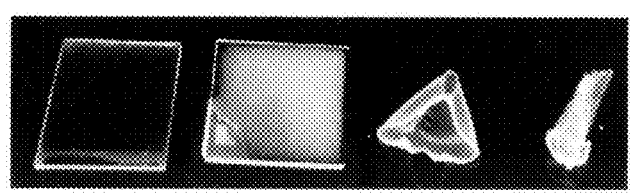
FIG. 8 is a photograph of an optical image of a bare glass slide ($1^{st}$ on the left), partially cured PDMS+Nanoparticle 1 (NP1) on a glass substrate ($2^{nd}$ on the left), and free standing NOA+NP1 films ($3^{rd}$ and $4^{th}$ from the left side).
Figure 9:
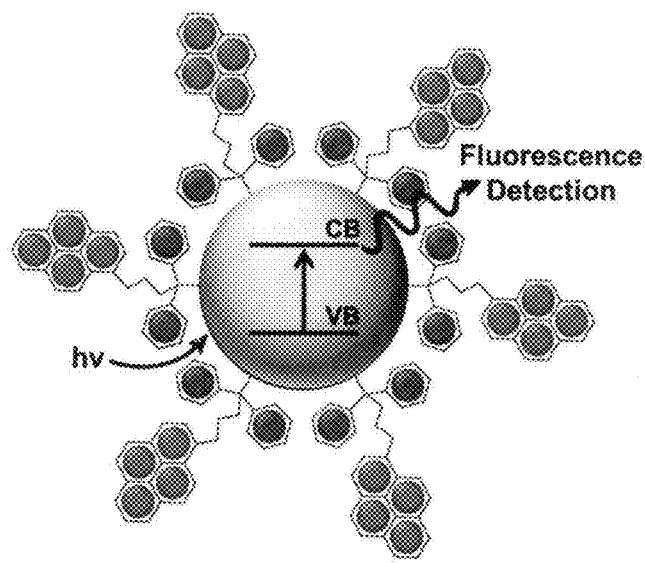
FIG. 9 is a schematic of the fluorescence process of a functionalized nanoparticle according to embodiments of the invention.
Figure 10:
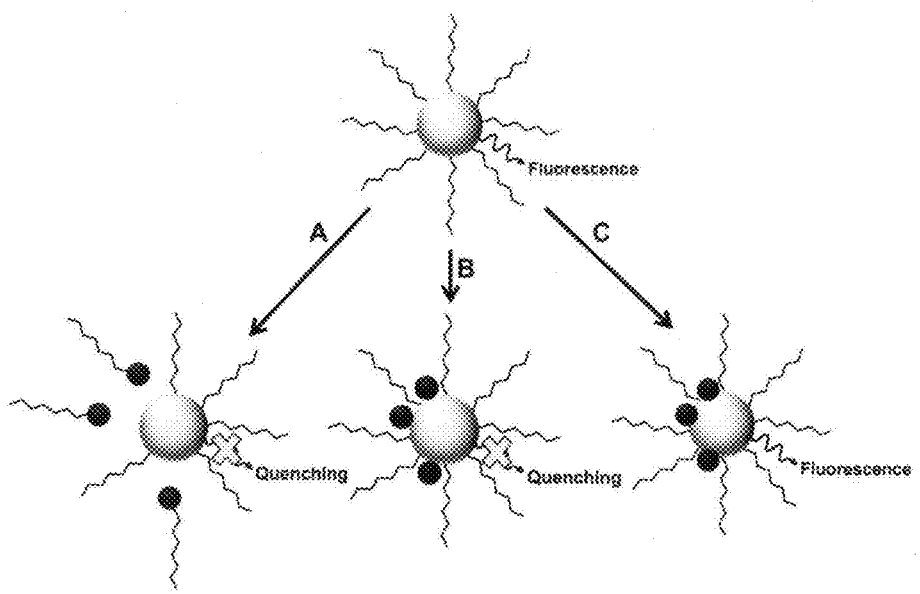
FIG. 10 is a schematic representation of various mechanisms for fluorescence changes of a functionalized nanoparticle according to embodiments of the invention.

Nanoparticles prepared as described in Example 2 were dissolved in a solution of chloroform (~100 mg/20 mL concentration) and added to host polymers consisting of polyurethane, polydimethyl siloxane, and SU-8 to fabricate free standing films on glass, silicon wafers, and silicon dioxide coated wafers. Where SU-8 is a negative photoresist that is epoxy based. SU-8 is composed of Bisphenol A Novolac epoxy that is dissolved in an organic solvent (gamma-butyrolactone GBL or cyclopentanone, depending on the formulation) and up to 10 wt. % of mixed Triarylsulfonium/hexafluoroantimonate salt as the photoacid generator). Polydimethyl siloxane (mixed 10:1 polymer to curing agent) was mixed with different volumes (1 mL up to 10 mL) forming a 1 to 10% solution by volume to form luminescent free standing films. Another mixture used polyurethane and SU-8 to form films as thin as 200 nm up to 5 microns thick. FIG. 8 shows several examples of the fluorescent films under UV-irradiation both on wafers and as stand-alone films.

The fluorescent nanoparticles of the present invention are made from varying ratios of metals including zinc, silver, copper and indium. By varying the ratios of the metals the nanoparticles can be synthesized to emit over a large range of the visible spectrum. Mixing these nanoparticles with a polymer to create a coating or a paint that can be applied to a variety of surfaces can be used to create a thin film that can be placed on any surface.

The type of coating can be either water dispersible or a solvent dispersible system depending upon the needs for the application. The process of creating the nanoparticle containing coating or paint is a simple process comprising:

1) choosing fluorescent nanoparticles with the desired emission wavelength;

2) incorporation (mixing) of the fluorescent nanoparticles into a polymer and/or other materials needed in the coating such as an adhesive or binding agent, or a catalyst to aid in the curing process;

3) placing the uncured nanoparticle polymer mixture onto a desired surface; and, 4) curing the polymer for final application.

Another application of the nanoparticle containing coatings of the present invention is for increased visual awareness. Incorporation of fluorescent nanoparticles into a paint or coating can allow increased visualization of the object being painted under specific lighting conditions such as ultraviolet or black lighting.

Another embodiment of the present invention comprises the production of test strips containing non-toxic, air and water stable, fluorescent nanoparticles in a variety of configurations to allow for facile metal detection. By selectively functionalizing these nanoparticles and adjusting the chemical composition, we are able to methodically alter the band gap. These changes influence the type of charge transfer that takes place between the nanoparticle and target molecules. Charge transfer between a target molecule and the nanoparticle is readily identified by a colorimetric change allowing for a fast, simple, visual detection system. A preferred type of detection that would be anticipated would be an on/off detection where the user would be able to visually see fluorescence on the strip before contact with a sample then upon exposure to a certain metal the fluorescence would quench.

Synthetic modifications can be made to the ligands on the nanoparticle to allow for binding to a substrate as well as metal ion specific binding. Types of substrates include but are not limited to filter paper, litmus paper, silicon wafers, glass slides, plastics. These nanoparticles can be incorporated into a test strip material that will then be used for detection of metals in solution at concentrations as low as 1 ppm.

Example 14

Nanoparticles prepared as outlined in Example 2 were made and dissolved in a solution of chloroform (~100 mg/20 mL concentration). The nanoparticles were solution cast onto various substrates including but not limited to filter paper, litmus paper, silicon wafers, glass slides and plastics at a concentration from 0.1-40% by weight in chloroform to form the test strips. Samples were allowed to air dry under ambient conditions and subsequently exposed to metal solutions containing varying concentrations of metals including but not limited to Cu2+, Hg2+, chromate, dichromate, etc. at concentrations of 5 nM-5 mM. Fluorescence quenching was monitored using a UV-flashlight and observing quenching by eye as well as measuring quenching of the substrate using a fluorimeter.

The mechanism for fluorescence changing has been tried on substrates including glass, pH paper and filter paper. All three substrates have a visible change by eye when in contact with a concentrated (5 mM) solution of metal ions. Detection mechanisms include fluorescence quenching and emission shifting (color changing).

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A functionalized fluorescent nanoparticle consisting of a single selected molar ratio of at least three elemental components wherein two of the at least three elemental components are S and In, and wherein other at least three elemental components are selected from the group consisting of:

Zn, Ag, Cu, and combinations thereof;

wherein said functionalized fluorescent nanoparticle consisting of said single selected molar ratio of said at least three elemental components is functionalized with a ligand; and, wherein said nanoparticle undergoes a fluorescence change in the presence of one or more target analytes.

2. The functionalized fluorescent nanoparticle of claim 1 wherein the selected molar ratio of said at least three elemental components is selected dependent upon the one or more target analytes that are targeted such that the functionalized fluorescent nanoparticle undergoes said fluorescence change in the presence of the one or more targeted target analytes.

3. The functionalized fluorescent nanoparticle of claim 1 wherein said one or more target analytes comprise metal ions or polyatomic metal containing ions.

4. The nanoparticle of claim 3 wherein said target analytes comprise ions of one or more metals selected from the group consisting of Aluminum, Chromium, Manganese, Iron, Cobalt, Nickel, Copper, Zinc, Arsenic, Barium, Mercury, Lead, Cadmium, and combinations thereof.

5. The functionalized fluorescent nanoparticle of claim 3 wherein said target analytes comprise polyatomic metal containing ion(s) comprising one or more ions of Chromate, Dichromate, or combinations thereof.

6. The functionalized fluorescent nanoparticle of claim 1 having the formula $xZn:yM:2yIn:zS$;

where M is Ag or Cu;

where x is 0 to 10;

where y is 0.01 to 10; and, where z is 2y to 5y.

7. The functionalized fluorescent nanoparticle of claim 1 having the formula:

$$2*(1-x)Zn:xM:xIn:zS;$$

where M is Ag or Cu;

where $0 < x \leq 1$; and where z is 2x to 5x.

8. The functionalized fluorescent nanoparticle of claim 1 wherein said ligand comprises an alkyl amine, an alkyl thiol, phenanthroline, a bipyridine, glutathione, or acetylsalicylic acid.

9. The functionalized fluorescent nanoparticle of claim 8 wherein the ligand is independent of the one or more target analytes that are targeted.

10. The functionalized fluorescent nanoparticle of claim 8 wherein said ligand is an alkyl having the formula $$CH_3(CH_2)_xR$$

where R is $NH_3$ or SH; and, where x is 2 to 20.

11. The functionalized fluorescent nanoparticle of claim 1 wherein said fluorescence change is a quenching of fluorescence at a specific wavelength, an amplification of fluorescence at a specific wavelength, or a shift of fluorescence from a specific wavelength to a new specific wavelength.

12. The functionalized fluorescent nanoparticle of claim 11 wherein said specific wavelength is between 400 nm and 800 nm, wherein said specific wavelength is determined by said molar ratio of said at least three elemental components.

13. A method for the fluorescence detection of a predetermined target analyte comprising:
   providing a fluorescence sensing indicator comprising a plurality of said nanoparticles of claim 12;
   exposing said indicator to a potential source of said predetermined target analyte; and,
   detecting any fluorescence changes,
   wherein said sensing indicator has a characteristic fluorescence wavelength, and
   wherein said fluorescence changes when in the presence of the target analyte includes a quenching of fluorescence at said characteristic wavelength, an amplification of fluorescence at said characteristic wavelength, or a shift of fluorescence from said characteristic wavelength to a new wavelength.

14. The method of claim 13 wherein said sensing indicator further comprises one or more solvents.

15. The functionalized fluorescent nanoparticle of claim 1 wherein the S is present in an amount equimolar with a total combined amount of In and the other of the at least three elemental components.

* * * * *